United States Patent [19]
Scheele et al.

[11] Patent Number: 5,663,315
[45] Date of Patent: Sep. 2, 1997

[54] ISOLATED DNA ENCODING HUMAN GP2

[75] Inventors: George Scheele, Brookline, Mass.; Shin-Ichi Fukuoka, Kyoto, Japan

[73] Assignee: AlphaGene, Inc., Woburn, Mass.

[21] Appl. No.: 350,435

[22] Filed: Dec. 6, 1994

[51] Int. Cl.$^6$ ............ C07H 21/04; C07H 21/02; C12P 21/06; C12N 5/00
[52] U.S. Cl. ............ 536/23.5; 536/23.1; 536/24.1; 435/69.1; 435/325; 435/357; 435/252.33; 435/358; 435/365; 435/362; 436/518
[58] Field of Search ............ 436/518; 536/23.1, 536/23.5, 24.1; 435/69.1, 240.2

[56] References Cited

U.S. PATENT DOCUMENTS 5,436,169  7/1995  Iovanna et al. ............ 436/518

OTHER PUBLICATIONS

J. Biol. Chem. 249(23): 7420–7431, Dec. 10, 1974, "Studies on the Guinea Pig Pancreas," Alan Tartakoff et al.
Nature 256:495–497, 1975, "Continuous cultures of fused cells secreting antibody of predefined specificity," Kohler et al.
Eur. J. Immunol. 6:511, 1976, "Derivation of specific antibody-producing tissue culture and tumor lines by cell fusion," Kohler et al.
J. Cell Biol. 77:288–314, 1978, "Sulfated Compounds in the Zymogen Granules of the Guinea Pig Pancreas," Hubert A. Reggio et al.
Proc. Natl. Acad. Sci, USA 80:4379–4383, Jul. 1983, "Comparison of secretory protein and memberane composition of secretory granules isolated from normal and neoplastic pancreatic acinar cells of rats," Linnea J. Hansen.
Gene 33:351–359, 1985, "Nucleotide sequence of a major class-III phage-T3 RNA-polymerase promotor located at 98.0% of phage-T3 genetic map," Sarkar et al.
Biochem. J. 225:481–486, Jan., 1985, "Localization of Tamm-Horsfall-glycoprotein-like immunoreactivity cultured bab-hamster kidney cells, shown by immunofluorescence and light-and electron–microscopic immuno–peroxidase techniques," Krishan L. Sikri et al.
Eur. J. Cell Biol. 39:70–76, Nov., 1985, "Membrane detachment and release of the major membrane glycoprotein of secretory granules in rat pancreatic exocrine cells," Johan R. Havings et al.
Clinica Chimica Acta 162:329–340, Feb. 15, 1987, "Uromucoid (Tamm–Horsfall glycoprotein) forms different polymeric arrangements on a filter surface under different physiochemical conditions," Roger C. Wiggins.
Proc. Natl. Acad. Sci. USA 84(14):4767–4771, 1987, "DNA sequence analysis with a modified bacteriophage 17 DNA polymerase," Tabor and Richardson.
Science 236:83–88, Apr. 3, 1987, "Identification of Human Uromodulin as the Tam–Horsfall Urinary Glycoprotein," Diane Pennica et al.
Scand J Urol Nephrol 22(4):313–315, 1988, "Scanning Electron Microscopy of Human Urine and Purified Tamm–Horsfall's Glycoprotein," Roger Bjugn et al.

Biochem. Biophys. Res. Comm. 154:1189–96, 1988, "A simple, Sensitive Bioassay for the Detection of Interleukin–1 Using Human Melanoma A375 Cell Line," Nakai et al.
Gene 67:31–40, 1988, "Single–step purification of polypeptides expressed in Escherichia coli as fusions with glutathione S–tranferase," Smith and Johnson.
Biochem. Biophys. Res. Comm. 154(2):818–823, Jul. 29, 1988, "The Major Protein of Pancreatic Zymogen Granule (GP–2) is Anchored Via Covalent Bonds to Phosphatidylinositol," Denis Lebel et al.
Pancreas5(1):1–7, 1990, "Rapid and Selective Cloning of Monitor Peptide, a Novel Cholecystokinin–releasing Peptide, Using Minimal Amino Acid Sequence and the Polymerase Chain Reaction," Shin–ichi Fukuokda et al.
Nucleic Acids Research 18(9):5900, 1990, "Nucleotide sequence encoding the major glycoprotein (GP2) of rat pancreatic secretory (zymogen) granule membranes," Shin–Ichi Fukuoka et al.
Eur. J. Cell Biol. 53(1):154–163, Oct. 1990, "The pancreatic membrane protein GP–2 localizes specifically to secretory granules and is shed into the pancreatic juice as a protein aggregate," Michael J. Rindler et al.
J. Biol. Chem. 265(34):20784–20789, Dec. 5, 1990, "Urododulin (Tamm–Horsfall Glycoprotein/Uromucoid) is a Phosphatidylinositol–linked Membrane Protein," Michael J. Rindler et al.
J. Histochem. Cytochem. 39(5):575–588,1991, "Ultrastructural Localization of GP2 in Acinar Cells of Pancreas: Presence of GP2 in Endocyctic and Exocytic Compartments," Adrien R. Beaudoin et al.
Proc. Natl. Acad. Sci. USA 88(7):2898–2902, Apr., 1991, "A single gene encodes membrane–bound and free forms of GP–2, the major glycoprotein in pancreatic secretory (zymogen) granule membranes", Shin–ichi Fukuoka et al.
Proc. Natl. Acad. Sci. USA 89:1189–1193, Feb. 15, 1992, "GP–2/THP gene family encodes self–binding glycosylphosphatidylinositol–anchored proteins in apical secretory compartments of pancreas and kidney," Shin–Ichi Fukuoka et al.
Eur. J. Cell Biol. 57:155–164, Apr. 1992, "Cytochemical and Immunocytochemical characterization of a fibrillar network (GP2) in pancreatic juice: possible role as a sieve in the pancreatic ductal systeml" Gilles Grondin et al.

(List continued on next page.)

*Primary Examiner*—James C. Housel
*Assistant Examiner*—Jennifer Shaver
*Attorney, Agent, or Firm*—Fish & Richardson P.C.

[57] ABSTRACT

The invention features a method for diagnosis of pancreatitis by detecting an elevation in the amount of GP2 pancreatic glycoprotein in a sample of bodily fluid such as human blood, serum, or urine. The invention also features isolated DNA encoding human GP2, a method for producing recombinant human GP2, antibodies which specifically bind to human GP2, a method for producing anti-human GP2 antibodies, and a kit for use in the diagnosis of pancreatitis.

13 Claims, 2 Drawing Sheets

OTHER PUBLICATIONS

Eur. J. Cell Biol. 58:259–270, Aug., 1992, "Characterization of pancreatic exocrine secretion produced by venom from the Brazillian scorpion, Tityus serrulatus," Paul L. Fletcher et al.

Eur. J. Cell Biol. 58(2):243–258, Aug. 1992, "The major zymogen granule membrane protein GP-2 in the rat pancreas is not involved in granule formation," Andrea Dittie et al.

J. Clin, Invest. 92:83–90, Jul., 1993, "GP2, the Homologue to the Renal Cast Protein Uromodulin, is a Major Component of Intraductal Plugs in Chronic Pancreatitis," Steven D. Freedman et al.

Eur. J. Cell Biol. 61:229–238, Aug., 1993, "Reversible pH–induced homophilic binding of GP2, a glycosyl–phosphatidylinositol–anchored protein in pancreatic zymogen granule membranes," Steven D. Freedman et al.

Pancreas9(2):139–149, 1994, "Role of the GP2/THP Family of GPI–Anchored Proteins in Membrane Trafficking During Regulated Exocrine Secretion," George A. Scheele et al.

Annals N.Y. Acad. Sci. 713:199–206, 1994, "Acid–Base Interactions during Exocrine Pancreatic Secretion," Freedman et al.

Journal of Biol. chem. 249(23):7420–7431, Dec. 1974, "Studies on the Guinea Pig Pancreas," Alan Tartakoff et al.

Jour. Biol. Chem. 266(36):24664–24669, Dec. 1991, "Messenger RNA Sequence and Expression of Rat Pancreatitis–assoicated Protein, a Lectin–related Protein Overexpressed during Acute Experimental Pancreatitis," Juan Iovanna et al.

Amer. Soc. Clin. Invest.76(4):2115–2126, Dec. 1985, "Isolation, Characterization, and Distribution of an Unusual Pancreatic Human Secretory Protein," Gross et al.

J. Clin. Invest. 84(1): 100–106, Jul.1989, "Secretory Pancratic Stone Protein Messenger RNA, Nucleotide Sequence and Expression in Chronic Calcifying Pancreatitis," Dominique Giorgi et al.

J. Clin. Invest. 90(6):2284–2291, Dec. 1992, "Human Pancreatitis–associated Protein: Messenger RNA Cloning and Expression in Pancreatic Diseases," Beatrice Orelle et al.

Biochemical and Biophysical Research Communications 110(1)6:69–74, Jan. 14, 1983, "Pancreatic Stone Protein, A phosphoprotein which Inhibits Calcium Carbonate Precipitation From Human Pancreatic Juice," Luc Multigner et al.

Eur. J. Biochem. 168(1):201–207, Oct. 1987, "Complete amino acid sequence of an immunoreactive form of human pancreatic stone protein isolated from pancreatic juice," Alain M. De Caro et al.

Pancreas 4(6):680–689, 1989, "Pancreatic Stone Protein: Quantification in Pancreatic Juice by Enzyme–Linked Immunosorbent Assay and Comparison with Other Methods," M. Provansal–Cheylan et al.

Hoops and Rindler, Isolation of the cDNA Encoding Glycoprotein–2 (GP–2), the Major Zymogen Granule Membrane Protein, Journal of Biological Chemistry 266:4257–4263, 1991.

Panozzo et al., Diagnostic Utility of a New Monoclonal Antibody Pancreatic Isoamylase Assay in Chronic Pancreatic Diseases, J. Clin. Chem. Clin. Biochem. 28:485–488, 1990.

Orelle et al. J. Clin. Invest. 1992 vol. 90: 2284–2291.

Nishimura et al. Abstract Accession No. 92388094 1992.

Alan Tartakoff et al., "Studies on the Guinea Pig Pancreas," J. Biol. Chem. 249(23): 7420–7431, Dec. 10, 1974.

Kohler et al., "Continuous cultures of fused cells secreting antibody of predefined specificity," Nature 256:495–497, 1975.

Kohler et al., "Derivation of specific antibody–producing tissue culture and tumor lines by cell fusion," Eur. J. Immunol. 6:511, 1976.

Hubert A. Reggio et al., "Sulfated Compounds in the Zymogen Granules of the Guinea Pig Pancreas," J. Cell Biol. 77:288–314, 1978.

Linnea J. Hansen, "Comparison of secretory protein and membrane composition of secretory granules isolated from normal and neoplastic pancreatic acinar cells of rats," Proc. Natl. Acad. Sci. USA 80:4379–4383, Jul. 1983.

Krishan L. Sikri et al., "Localization of Tamm–Horsfall–glycoprotein–like immunoreactivity in cultured baby–hamster kidney cells, shown by immunofluorescence and light–and electron–microscopic immunoperoxidase techniques," Biochem. J. 225:481–486, Jan., 1985.

Sarkar et al., "Nucleotide sequence of a major class–III phage–T3 RNA–polymerase promoter located at 98.0% of phage–T3 genetic map," Gene 33:351–359, 1985.

Johan R. Havinga et al., "Membrane detachment and release of the major membrane glycoprotein of secretory granules in rat pancreatic exocrine cells," Eur. J. Cell Biol. 39:70–76, Nov., 1985.

Roger C. Wiggins, "Uromucoid (Tamm–Horsfall glycoprotein) forms different polymeric arrangements on a filter surface under different physicochemical conditions," Clinica Chimica Acta 162:329–340, Feb. 15, 1987.

Tabor and Richardson, "DNA sequence analysis with a modified bacteriophage T7 DNA polymerase," Proc. Natl. Acad. Sci. USA 84(14):4767–4771, 1987.

Diane Pennica et al., "Identification of Human Uromodulin as the Tam–Horsfall Urinary Glycoprotein," Science 236:83–88, Apr. 3, 1987.

Roger Bjugn et al., "Scanning Electron Microscopy of Human Urine and Purified Tamm–Horsfall's Glycoprotein," Scand J Urol Nephrol 22(4):313–315, 1988.

Nakai et al., "A Simple, Sensitive Bioassay for the Detection of Interleukin–1 Using Human Melanoma A375 Cell Line," Biochem. Biophys. Res. Comm. 154:1189–96, 1988.

Smith and Johnson, "Single–step purification of polypeptides expressed in Escherichia coli as fusions with glutathione S–tranferase," Gene 67:31–40, 1988.

Denis Lebel et al., "The Major Protein of Pancreatic Zymogen Granule Membranes (GP–2) is Anchored Via Covalent Bonds to Phosphatidylinositol," Biochem. Biophys. Res. Comm. 154(2):818–823, Jul. 29, 1988.

Shin–Ichi Fukuoka et al., "Rapid and Selective Cloning of Monitor Peptide, a Novel Cholecystokinin–releasing Peptide, Using Minimal Amino Acid Sequence and the Polymerase Chain Reaction," Pancreas 5(1):1–7, 1990.

Shin–Ichi Fukuoka et al., "Nucleotide sequence encoding the major glycoprotein (GP2) of rat pancreatic secretory (zymogen) granule membranes," Nucleic Acids Research 18(19):5900, 1990.

Michael J. Rindler et al., "The pancreatic membrane protein GP–2 localizes specifically to secretory granules and is shed into the pancreatic juice as a protein aggregate," Eur. J. Cell Biol. 53(1):154–163, Oct., 1990.

Michael J. Rindler et al., "Uromodulin (Tamm–Horsfall Glycoprotein/Uromucoid) is a Phosphatidylinositol–linked Membrane Protein," J. Biol. Chem. 265(34):20784–20789, Dec. 5, 1990.

Adrien R. Beaudoin et al., "Ultrastructural Localization of GP2 in Acinar Cells of Pancreas: Presence of GP2 in Endocytic and Exocytic Compartments," *J. Histochem. Cytochem.* 39(5):575–588, 1991.

Shin–Ichi Fukuoka et al., "A single gene encodes membrane–bound and free forms of GP–2, the major glycoprotein in pancreatic secretory (zymogen) granule membranes," *Proc. Natl. Acad. Sci. USA* 88(7):2898–2902, Apr., 1991.

Shin–Ichi Fukuoka et al., "GP–2/THP gene family encodes self–binding glycosylphosphatidylinositol–anchored proteins in apical secretory compartments of pancreas and kidney," *Proc. Natl. Acad. Sci. USA* 89:1189–1193, Feb. 15, 1992.

Gilles Grondin et al., "Cytochemical and Immunocytochemical characterization of a fibrillar network (GP2) in pancreatic juice: possible role as a sieve in the pancreatic ductal system," *Eur. J. Cell Biol.* 57:155–164, Apr., 1992.

Paul L. Fletcher et al., "Characteristics of pancreatic exocrine secretion produced by venom from the Brazilian scorpion, *Tityus serrulatus*," *Eur. J. Cell Biol.* 58:259–270, Aug., 1992.

Andrea Dittie et al., "The major zymogen granule membrane protein GP-2 in the rat pancreas is not involved in granule formation," *Eur. J. Cell Biol.* 58(2):243–258, Aug., 1992.

Steven D. Freedman et al., "GP2, the Homolgue to the Renal Cast Protein Uromodulin, is a Major Component of Intraductal Plugs in Chronic Pancreatitis," *J. Clin. Invest.* 92:83–90, Jul., 1993.

Steven D. Freedman et al., "Reversible pH–induced homophilic binding of GP2, a glycosyl–phosphatidylinositol–anchored protein in pancreatic zymogen granule membranes," *Eur. J. Cell Biol.* 61:229–238, Aug. 1993.

George A. Scheele et al., "Role of the GP2/THP Family of GPI–Anchored Proteins in Membrane Trafficking During Regulated Exocrine Secretion," *Pancreas* 9(2):139–149, 1994.

Freedman et al., "Acid–Base Interactions during Exocrine Pancreatic Secretion," *Annals N.Y. Acad. Sci.* 713:199–206, 1994.

Alan Tartakoff et al., "Studies on the Guinea Pig Pancreas," *J. Biol. Chem.* 249(23): 7420–7431, Dec. 10, 1974.

Kohler et al., "Continuous cultures of fused cells secreting antibody of predefined specificity," *Nature* 256:495–497, 1975.

Kohler et al., "Derivation of specific antibody–producing tissue culture and tumor lines by cell fusion," *Eur. J. Immunol.* 6:511, 1976.

| | | | | | | | | | | | | | | | | |
|---|---|---|---|---|---|---|---|---|---|---|---|---|---|---|---|---|
| ATG | GTG | GGC | TCT | GGC | CTC | CTG | TGG | CTG | GCC | TTG | GTC | TCC | TGC | ATT | CTG | 48 |
| Met | Val | Gly | Ser | Gly | Leu | Leu | Trp | Leu | Ala | Leu | Val | Ser | Cys | Ile | Leu | |
| 1 | | | | 5 | | | | | 10 | | | | | 15 | | |
| ACC | CAG | GCA | TCT | GCA | GTG | CAG | CGA | GTT | CCA | CGA | GAC | CCA | TCC | ACT | GTG | 96 |
| Thr | Gln | Ala | Ser | Ala | Val | Gln | Arg | Val | Pro | Arg | Asp | Pro | Ser | Thr | Val | |
| | | | 20 | | | | 25 | | | | | 30 | | | | |
| GAG | GAC | AAA | AAG | TGT | GAG | AAG | GCC | TGC | CGC | CCC | GAG | GAG | GAG | TGC | CTT | 144 |
| Glu | Asp | Lys | Lys | Cys | Glu | Lys | Ala | Cys | Arg | Pro | Glu | Glu | Glu | Cys | Leu | |
| | | 35 | | | | 40 | | | | | 45 | | | | | |
| GCC | CTC | AAC | AGC | ACC | TGG | GGC | TGT | TTC | TGC | AGA | CAG | GAC | CTC | AAT | AGT | 192 |
| Ala | Leu | Asn | Ser | Thr | Trp | Gly | Cys | Phe | Cys | Arg | Gln | Asp | Leu | Asn | Ser | |
| | 50 | | | | | 55 | | | | | 60 | | | | | |
| TCT | GAT | GTC | CAC | AGT | TTG | CAG | CCT | CAG | CTA | GAC | TGT | GGG | CCC | AGG | GAG | 240 |
| Ser | Asp | Val | His | Ser | Leu | Gln | Pro | Gln | Leu | Asp | Cys | Gly | Pro | Arg | Glu | |
| 65 | | | | | 70 | | | | | 75 | | | | | 80 | |
| ATC | AAG | GTG | AAG | GTG | GAC | AAA | TGT | TTG | CAG | GGA | GGC | CTG | GGT | TTC | CCG | 288 |
| Ile | Lys | Val | Lys | Val | Asp | Lys | Cys | Leu | Gln | Gly | Gly | Leu | Gly | Phe | Pro | |
| | | | | 85 | | | | | 90 | | | | | 95 | | |
| GAG | GAG | GTC | ATT | GCC | TAC | CTG | CGA | GAC | CCA | AAC | TGC | AGC | AGC | ATC | TTG | 336 |
| Glu | Glu | Val | Ile | Ala | Tyr | Leu | Arg | Asp | Pro | Asn | Cys | Ser | Ser | Ile | Leu | |
| | | | 100 | | | | | 105 | | | | | 110 | | | |
| CAG | ACA | GAG | GAG | AGG | AAC | TGG | GTA | TCT | GTG | ACC | AGC | CCC | GTC | CAG | GCT | 384 |
| Gln | Thr | Glu | Glu | Arg | Asn | Trp | Val | Ser | Val | Thr | Ser | Pro | Val | Gln | Ala | |
| | | | 115 | | | | | 120 | | | | | 125 | | | |
| AGT | GCC | TGC | AGG | AAC | ATT | CTG | GAG | AGA | AAT | CAA | ACC | CAT | GCC | ATC | TAC | 432 |
| Ser | Ala | Cys | Arg | Asn | Ile | Leu | Glu | Arg | Asn | Gln | Thr | His | Ala | Ile | Tyr | |
| | 130 | | | | | 135 | | | | | 140 | | | | | |
| AAA | AAC | ACC | CTC | TCC | TTG | GTC | AAT | GAT | TTC | ATC | ATA | AGA | GAC | ACC | ATC | 480 |
| Lys | Asn | Thr | Leu | Ser | Leu | Val | Asn | Asp | Phe | Ile | Ile | Arg | Asp | Thr | Ile | |
| 145 | | | | | 150 | | | | | 155 | | | | | 160 | |
| CTC | AAC | ATC | AAC | TTC | CAA | TGT | GCC | TAC | CCA | CTG | GAC | ATG | AAA | GTC | AGC | 528 |
| Leu | Asn | Ile | Asn | Phe | Gln | Cys | Ala | Tyr | Pro | Leu | Asp | Met | Lys | Val | Ser | |
| | | | | 165 | | | | | 170 | | | | | 175 | | |
| CTC | CAA | GCT | GCC | TTG | CAG | CCC | ATT | GTA | AGT | TCC | CTG | AAC | GTC | AGT | GTG | 576 |
| Leu | Gln | Ala | Ala | Leu | Gln | Pro | Ile | Val | Ser | Ser | Leu | Asn | Val | Ser | Val | |
| | | | 180 | | | | | 185 | | | | | 190 | | | |
| GAC | GGG | AAT | GGA | GAG | TTC | ATT | GTC | AGG | ATG | GCC | CTC | TTC | CAA | GAC | CAG | 624 |
| Asp | Gly | Asn | Gly | Glu | Phe | Ile | Val | Arg | Met | Ala | Leu | Phe | Gln | Asp | Gln | |
| | | | 195 | | | | | 200 | | | | | 205 | | | |

FIG. 1A

```
AAC TAC ACG AAT CCT TAC GAA GGG GAT GCA GTT GAA CTG TCT GTT GAG    672
Asn Tyr Thr Asn Pro Tyr Glu Gly Asp Ala Val Glu Leu Ser Val Glu
    210             215             220

TCC GTC CTG TAT GTG GGT GCC ATC TTG GAA CAA GGG GAC ACC TCC CGG    720
Ser Val Leu Tyr Val Gly Ala Ile Leu Glu Gln Gly Asp Thr Ser Arg
225             230             235             240

TTT AAC CTG GTG TTG AGG AAC TGC TAC GCC ACC CCC ACT GAA GAC AAG    768
Phe Asn Leu Val Leu Arg Asn Cys Tyr Ala Thr Pro Thr Glu Asp Lys
                245             250             255

GCT GAC CTT GTG AAG TAT TTC ATC ATC AGA AAC AGC TGC TCA AAT CAA    816
Ala Asp Leu Val Lys Tyr Phe Ile Ile Arg Asn Ser Cys Ser Asn Gln
            260             265             270

CGT GAT TCC ACC ATC CAC GTG GAG GAG AAT GGG CAG TCC TCG GAA AGC    864
Arg Asp Ser Thr Ile His Val Glu Glu Asn Gly Gln Ser Ser Glu Ser
        275             280             285

CGG TTC TCA GTC CAG ATG TTC ATG TTT GCT GGA CAT TAT GAC CTA GTT    912
Arg Phe Ser Val Gln Met Phe Met Phe Ala Gly His Tyr Asp Leu Val
    290             295             300

TTC CTG CAT TGT GAG ATT CAT CTC TGT GAT TCT CTT AAT GAA CAG TGC    960
Phe Leu His Cys Glu Ile His Leu Cys Asp Ser Leu Asn Glu Gln Cys
305             310             315             320

CAG CCT TCT TGC TCA AGA AGT CAA GTC CGC AGT GAA GTA CCG GCC ATC   1008
Gln Pro Ser Cys Ser Arg Ser Gln Val Arg Ser Glu Val Pro Ala Ile
                325             330             335

GAC CTA GCC CGG GTT CTA GAT TTG GGG CCC ATC ACT CGG AGA GGT GGA   1056
Asp Leu Ala Arg Val Leu Asp Leu Gly Pro Ile Thr Arg Arg Gly Gly
            340             345             350

CAG TCT CCC GGT GTC ATG AAT GGA ACC CCT AGC ACT GCA GGG TTC CTG   1104
Gln Ser Pro Gly Val Met Asn Gly Thr Pro Ser Thr Ala Gly Phe Leu
        355             360             365

GTG GCC TGG CCT ATG GTC CTC CTG ACT GTC CTC CTG GCT TTG GCT GTC   1152
Val Ala Trp Pro Met Val Leu Leu Thr Val Leu Leu Ala Leu Ala Val
    370             375             380

TGA
```

FIG. 1B

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1155 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 1..1152

( x i ) SEQUENCE DESCRIPTION: SEQ ID NO:1:

```
ATG  GTG  GGC  TCT  GGC  CTC  CTG  TGG  CTG  GCC  TTG  GTC  TCC  TGC  ATT  CTG       48
Met  Val  Gly  Ser  Gly  Leu  Leu  Trp  Leu  Ala  Leu  Val  Ser  Cys  Ile  Leu
  1                    5                        10                       15

ACC  CAG  GCA  TCT  GCA  GTG  CAG  CGA  GTT  CCA  CGA  GAC  CCA  TCC  ACT  GTG       96
Thr  Gln  Ala  Ser  Ala  Val  Gln  Arg  Val  Pro  Arg  Asp  Pro  Ser  Thr  Val
                      20                       25                       30

GAG  GAC  AAA  AAG  TGT  GAG  AAG  GCC  TGC  CGC  CCC  GAG  GAG  GAG  TGC  CTT      144
Glu  Asp  Lys  Lys  Cys  Glu  Lys  Ala  Cys  Arg  Pro  Glu  Glu  Glu  Cys  Leu
              35                       40                       45

GCC  CTC  AAC  AGC  ACC  TGG  GGC  TGT  TTC  TGC  AGA  CAG  GAC  CTC  AAT  AGT      192
Ala  Leu  Asn  Ser  Thr  Trp  Gly  Cys  Phe  Cys  Arg  Gln  Asp  Leu  Asn  Ser
         50                       55                       60

TCT  GAT  GTC  CAC  AGT  TTG  CAG  CCT  CAG  CTA  GAC  TGT  GGG  CCC  AGG  GAG      240
Ser  Asp  Val  His  Ser  Leu  Gln  Pro  Gln  Leu  Asp  Cys  Gly  Pro  Arg  Glu
 65                       70                       75                       80

ATC  AAG  GTG  AAG  GTG  GAC  AAA  TGT  TTG  CAG  GGA  GGC  CTG  GGT  TTC  CCG      288
Ile  Lys  Val  Lys  Val  Asp  Lys  Cys  Leu  Gln  Gly  Gly  Leu  Gly  Phe  Pro
                           85                       90                       95

GAG  GAG  GTC  ATT  GCC  TAC  CTG  CGA  GAC  CCA  AAC  TGC  AGC  AGC  ATC  TTG      336
Glu  Glu  Val  Ile  Ala  Tyr  Leu  Arg  Asp  Pro  Asn  Cys  Ser  Ser  Ile  Leu
                   100                      105                      110

CAG  ACA  GAG  GAG  AGG  AAC  TGG  GTA  TCT  GTG  ACC  AGC  CCC  GTC  CAG  GCT      384
Gln  Thr  Glu  Glu  Arg  Asn  Trp  Val  Ser  Val  Thr  Ser  Pro  Val  Gln  Ala
              115                      120                      125

AGT  GCC  TGC  AGG  AAC  ATT  CTG  GAG  AGA  AAT  CAA  ACC  CAT  GCC  ATC  TAC      432
Ser  Ala  Cys  Arg  Asn  Ile  Leu  Glu  Arg  Asn  Gln  Thr  His  Ala  Ile  Tyr
         130                      135                      140

AAA  AAC  ACC  CTC  TCC  TTG  GTC  AAT  GAT  TTC  ATC  ATA  AGA  GAC  ACC  ATC      480
Lys  Asn  Thr  Leu  Ser  Leu  Val  Asn  Asp  Phe  Ile  Ile  Arg  Asp  Thr  Ile
145                      150                      155                      160
```

```
CTC AAC ATC AAC TTC CAA TGT GCC TAC CCA CTG GAC ATG AAA GTC AGC       528
Leu Asn Ile Asn Phe Gln Cys Ala Tyr Pro Leu Asp Met Lys Val Ser
            165                 170                 175

CTC CAA GCT GCC TTG CAG CCC ATT GTA AGT TCC CTG AAC GTC AGT GTG       576
Leu Gln Ala Ala Leu Gln Pro Ile Val Ser Ser Leu Asn Val Ser Val
        180                     185                 190

GAC GGG AAT GGA GAG TTC ATT GTC AGG ATG GCC CTC TTC CAA GAC CAG       624
Asp Gly Asn Gly Glu Phe Ile Val Arg Met Ala Leu Phe Gln Asp Gln
            195                 200                 205

AAC TAC ACG AAT CCT TAC GAA GGG GAT GCA GTT GAA CTG TCT GTT GAG       672
Asn Tyr Thr Asn Pro Tyr Glu Gly Asp Ala Val Glu Leu Ser Val Glu
    210                 215                 220

TCC GTC CTG TAT GTG GGT GCC ATC TTG GAA CAA GGG GAC ACC TCC CGG       720
Ser Val Leu Tyr Val Gly Ala Ile Leu Glu Gln Gly Asp Thr Ser Arg
225                 230                 235                 240

TTT AAC CTG GTG TTG AGG AAC TGC TAC GCC ACC CCC ACT GAA GAC AAG       768
Phe Asn Leu Val Leu Arg Asn Cys Tyr Ala Thr Pro Thr Glu Asp Lys
            245                 250                 255

GCT GAC CTT GTG AAG TAT TTC ATC ATC AGA AAC AGC TGC TCA AAT CAA       816
Ala Asp Leu Val Lys Tyr Phe Ile Ile Arg Asn Ser Cys Ser Asn Gln
        260                 265                 270

CGT GAT TCC ACC ATC CAC GTG GAG GAG AAT GGG CAG TCC TCG GAA AGC       864
Arg Asp Ser Thr Ile His Val Glu Glu Asn Gly Gln Ser Ser Glu Ser
    275                 280                 285

CGG TTC TCA GTC CAG ATG TTC ATG TTT GCT GGA CAT TAT GAC CTA GTT       912
Arg Phe Ser Val Gln Met Phe Met Phe Ala Gly His Tyr Asp Leu Val
290                 295                 300

TTC CTG CAT TGT GAG ATT CAT CTC TGT GAT TCT CTT AAT GAA CAG TGC       960
Phe Leu His Cys Glu Ile His Leu Cys Asp Ser Leu Asn Glu Gln Cys
305                 310                 315                 320

CAG CCT TCT TGC TCA AGA AGT CAA GTC CGC AGT GAA GTA CCG GCC ATC      1008
Gln Pro Ser Cys Ser Arg Ser Gln Val Arg Ser Glu Val Pro Ala Ile
            325                 330                 335

GAC CTA GCC CGG GTT CTA GAT TTG GGG CCC ATC ACT CGG AGA GGT GGA      1056
Asp Leu Ala Arg Val Leu Asp Leu Gly Pro Ile Thr Arg Arg Gly Gly
        340                 345                 350

CAG TCT CCC GGT GTC ATG AAT GGA ACC CCT AGC ACT GCA GGG TTC CTG      1104
Gln Ser Pro Gly Val Met Asn Gly Thr Pro Ser Thr Ala Gly Phe Leu
        355                 360                 365

GTG GCC TGG CCT ATG GTC CTC CTG ACT GTC CTC CTG GCT TTG GCT GTC      1152
Val Ala Trp Pro Met Val Leu Leu Thr Val Leu Leu Ala Leu Ala Val
370                 375                 380

TGA                                                                  1155
```

( 2 ) INFORMATION FOR SEQ ID NO:2:

( i ) SEQUENCE CHARACTERISTICS:
( A ) LENGTH: 384 amino acids
( B ) TYPE: amino acid
( D ) TOPOLOGY: linear ( i i ) MOLECULE TYPE: protein ( x i ) SEQUENCE DESCRIPTION: SEQ ID NO:2:

```
Met Val Gly Ser Gly Leu Leu Trp Leu Ala Leu Val Ser Cys Ile Leu
 1               5                  10                  15

Thr Gln Ala Ser Ala Val Gln Arg Val Pro Arg Asp Pro Ser Thr Val
            20                  25                  30

Glu Asp Lys Lys Cys Glu Lys Ala Cys Arg Pro Glu Glu Glu Cys Leu
        35                  40                  45
```

| | | | | | | | | | | | | | | |
|---|---|---|---|---|---|---|---|---|---|---|---|---|---|---|
| Ala | Leu 50 | Asn | Ser | Thr | Trp | Gly 55 | Cys | Phe | Cys | Arg | Gln 60 | Asp | Leu | Asn | Ser |
| Ser 65 | Asp | Val | His | Ser | Leu 70 | Gln | Pro | Gln | Leu | Asp 75 | Cys | Gly | Pro | Arg | Glu 80 |
| Ile | Lys | Val | Lys | Val 85 | Asp | Lys | Cys | Leu | Gln 90 | Gly | Gly | Leu | Gly | Phe 95 | Pro |
| Glu | Glu | Val | Ile 100 | Ala | Tyr | Leu | Arg | Asp 105 | Pro | Asn | Cys | Ser | Ser 110 | Ile | Leu |
| Gln | Thr | Glu 115 | Glu | Arg | Asn | Trp | Val 120 | Ser | Val | Thr | Ser | Pro 125 | Val | Gln | Ala |
| Ser | Ala 130 | Cys | Arg | Asn | Ile | Leu 135 | Glu | Arg | Asn | Gln | Thr 140 | His | Ala | Ile | Tyr |
| Lys 145 | Asn | Thr | Leu | Ser | Leu 150 | Val | Asn | Asp | Phe | Ile 155 | Ile | Arg | Asp | Thr | Ile 160 |
| Leu | Asn | Ile | Asn | Phe 165 | Gln | Cys | Ala | Tyr | Pro 170 | Leu | Asp | Met | Lys | Val 175 | Ser |
| Leu | Gln | Ala | Ala 180 | Leu | Gln | Pro | Ile | Val 185 | Ser | Ser | Leu | Asn | Val 190 | Ser | Val |
| Asp | Gly | Asn 195 | Gly | Glu | Phe | Ile | Val 200 | Arg | Met | Ala | Leu | Phe 205 | Gln | Asp | Gln |
| Asn | Tyr 210 | Thr | Asn | Pro | Tyr | Glu 215 | Gly | Asp | Ala | Val | Glu 220 | Leu | Ser | Val | Glu |
| Ser 225 | Val | Leu | Tyr | Val | Gly 230 | Ala | Ile | Leu | Glu | Gln 235 | Gly | Asp | Thr | Ser | Arg 240 |
| Phe | Asn | Leu | Val | Leu 245 | Arg | Asn | Cys | Tyr | Ala 250 | Thr | Pro | Thr | Glu | Asp 255 | Lys |
| Ala | Asp | Leu | Val 260 | Lys | Tyr | Phe | Ile | Ile 265 | Arg | Asn | Ser | Cys | Ser 270 | Asn | Gln |
| Arg | Asp | Ser 275 | Thr | Ile | His | Val | Glu 280 | Glu | Asn | Gly | Gln | Ser 285 | Ser | Glu | Ser |
| Arg | Phe 290 | Ser | Val | Gln | Met | Phe 295 | Met | Phe | Ala | Gly | His 300 | Tyr | Asp | Leu | Val |
| Phe 305 | Leu | His | Cys | Glu | Ile 310 | His | Leu | Cys | Asp | Ser 315 | Leu | Asn | Glu | Gln | Cys 320 |
| Gln | Pro | Ser | Cys | Ser 325 | Arg | Ser | Gln | Val | Arg 330 | Ser | Glu | Val | Pro | Ala 335 | Ile |
| Asp | Leu | Ala | Arg 340 | Val | Leu | Asp | Leu | Gly 345 | Pro | Ile | Thr | Arg | Arg 350 | Gly | Gly |
| Gln | Ser | Pro 355 | Gly | Val | Met | Asn | Gly 360 | Thr | Pro | Ser | Thr | Ala 365 | Gly | Phe | Leu |
| Val | Ala 370 | Trp | Pro | Met | Val | Leu 375 | Leu | Thr | Val | Leu | Leu 380 | Ala | Leu | Ala | Val |

ISOLATED DNA ENCODING HUMAN GP2

BACKGROUND OF THE INVENTION

The invention relates to methods of diagnosing pancreatitis.

The pancreas is a large, elongated gland situated transversely behind the stomach, between the spleen and the duodenum. The pancreas consists of two portions, both of which are crucial for regulation of metabolism and for digestion. The endocrine portion of the pancreas (pars endocrina), which contains the islets of Langerhans, produces and secretes both insulin and glucagon directly into the bloodstream. These two hormones play a major role in the regulation of carbohydrate metabolism. The exocrine portion of the pancreas (pars exocrina) consists of secretory units (pancreatic acini) which produce and secrete pancreatic juice into the pancreatic duct and thence into the duodenum. Pancreatic juice contains approximately twenty known enzymes and isoenzymes, including glycosidase, proteases, lipases, and nucleases, which are essential for digestion of carbohydrates, fats, proteins, and other food components.

Pancreatitis is an inflammation of the pancreas accompanied by autodigestion of pancreatic tissue by its own enzymes. Pancreatitis may be either acute or chronic. Acute pancreatitis is associated with a sudden onset of abdominal pain, nausea, and vomiting. Predisposing conditions for acute pancreatitis include chronic alcoholism, gallstones, hypercalcemia, hyperlipoproteinemia, blunt abdominal trauma, and penetrating peptic ulcer. Predisposition may also be inherited as an autosomal dominant trait.

Chronic pancreatitis, which may be accompanied by recurrent attacks of acute pancreatitis, is usually associated with recurrent, chronic abdominal pain, progressive fibrosis and loss of exocrine (steatorrhea) and endocrine (diabetes mellitus) function, though the disease may also be asymptomatic. Although the specific pathogenesis of chronic pancreatitis is unknown, most cases of the disease suggest that obstruction of the pancreatic ducts may play a crucial role. Forms of acute or chronic pancreatitis include acute hemorrhagic pancreatitis, chronic calcific (calcareous) pancreatitis, centrilobular pancreatitis, chronic relapsing pancreatitis, perilobular pancreatitis, and purulent pancreatitis.

The majority of individuals who develop acute or chronic pancreatitis are alcoholics. Pancreatitis may also result from a slow-growing mucinous pancreatic cystadenoma or congenital anomalies such as annular pancreas or pancreas divisum, presumably as a result of intermittent ductular obstruction. Occasionally, infections that involve the pancreas, such as those caused by mumps virus, *Salmonella typhi*, or streptococci, produce an acute suppurative pancreatitis. Pancreatitis may also develop in malnourished individuals in the third world (tropical pancreatitis) and in response to an abrupt increase of food intake after prolonged fasting. Some evidence suggests a link between episodes of acute pancreatitis and a variety of drugs including azathioprine, thiazides, sulfonamides, furosemide, estrogens, tetracycline, and cytosine arabinoside. There is also some suggestion that corticosteroids, L-asparaginase, ethacrynic acid, phenformin, and procainamide may produce pancreatic inflammation.

Pancreatitis is conventionally diagnosed by physical examination and by evaluation of levels of amylase, lipase, or trypsin in serum, or the ratio of amylase to creatinine in serum. None of these conventional diagnostic tests is specific for pancreatitis. For example, increased serum amylase may also be due to cholecystitis, hepatitis, intestinal obstruction, mesenteric thrombosis, parotitis, perforated duodenal ulcer, or a ruptured aortic aneurysm. Increased levels of serum trypsin can be caused by chronic renal failure. Similarly, the ratio of amylase to creatinine in serum may be elevated by uremia or acute tubular damage.

SUMMARY OF THE INVENTION

In general, the invention features a method for diagnosis of pancreatitis by detecting an elevation in the level of pancreatic glycoprotein, GP2, in a sample of bodily fluid, such as human blood, serum, or urine. The invention also features isolated DNA encoding human GP2, a method for producing recombinant human GP2, antibodies which specifically bind to human GP2, a method for producing anti-human GP2 antibodies, and a kit for use in the diagnosis of pancreatitis.

In a preferred embodiment, a test sample of a patient's bodily fluid is contacted with an antibody which specifically binds to human GP2. The patient is diagnosed with pancreatitis when the amount of antibody binding to the test sample is significantly greater than the amount of antibody binding to a control sample (e.g., a sample taken from an unaffected individual).

In another embodiment, a test sample of a patient's bodily fluid is contacted with an antibody which specifically binds to human GP2. The sample is then incubated with detectably labeled GP2 to detect the level of antibody which remains unbound to endogenous, unlabelled GP2. The patient is diagnosed with pancreatitis when the amount of detectably labeled GP2 binding to the anti-GP2 antibody in the test sample is significantly less than the amount of detectably labeled GP2 binding to the anti-GP2 antibody added to a control sample, such as one taken from an unaffected individual.

In another embodiment, the amount of anti-human GP2 antibody bound to the test sample may be compared to the amount of binding of this antibody to a sample containing a known amount of human GP2 protein. The degree of severity of pancreatitis in the patient may then be assessed by determining an approximate amount of GP2 present in the test sample, or at least the amount relative to the standard.

Another aspect of the invention features isolated DNA (e.g., cDNA) encoding human GP2 polypeptide or an antigenic fragment thereof (e.g., SEQ ID NO:1 or a degenerate variant thereof). This DNA is preferably operably linked to a promoter sequence for expression of the GP2 polypeptide or fragment thereof. The DNA of the invention may encode a polypeptide having the amino acid sequence of SEQ ID NO:2, or a polypeptide having an amino acid sequence which differs from that of SEQ ID NO:2 solely by conservative amino acid substitutions. Preferably, the isolated DNA includes a nucleotide sequence which hybridizes under stringent hybridization conditions to a DNA having the sequence of SEQ ID NO:1.

Yet another aspect of the invention features a substantially pure human GP2 polypeptide (e.g. recombinant GP2, synthetic GP2, or naturally occurring GP2). Recombinant GP2 may be produced by (1) culturing a cell transformed with an isolated DNA encoding (a) human GP2 or (b) an antigenic fragment of human GP2, the DNA being positioned for expression in the cell, and the culturing being under conditions for expressing the DNA; and (2) isolating the polypeptide expressed.

Another aspect of the invention features an antibody which specifically binds human GP2, e.g., monoclonal antibody. The antibody may be produced by (1) immunizing a non-human mammal (e.g., a mouse, rabbit, or rat) with an antigen comprising human GP2 or an antigenic fragment thereof, and (2) isolating antibodies which bind to human GP2.

Yet another aspect of the invention features kits for detecting human GP2. In general, the kits include a vessel containing an antibody which specifically binds GP2, and which may be detectably labeled. If the anti-GP2 antibody is unlabelled, a second vessel containing a second antibody which is detectably labeled and which specifically binds the anti-GP2 antibody is preferably included. Where the detectable label is an enzyme, the kit further includes a third vessel containing a substrate for the enzyme.

In another embodiment of the invention, the kit for detecting human GP2 includes a vessel containing an antibody which specifically binds human GP2 and a vessel containing either detectably labeled human GP2 or a detectably labeled fragment of human GP2 which has an epitope that is specifically bound by the anti-GP2 antibody.

By "pancreatitis" is meant acute or chronic inflammation of the pancreas accompanied by autodigestion of pancreatic tissue by its own enzymes. Pancreatitis may be symptomatic or asymptomatic.

By "acute pancreatitis" is meant pancreatitis characterized by sudden onset of abdominal pain, nausea, and vomiting. Acute pancreatitis may occur in the setting of chronic pancreatitis.

By "chronic pancreatitis" is meant pancreatitis normally characterized by chronic recurrent abdominal pain, progressive fibrosis, and loss of exocrine and endocrine function. Chronic pancreatitis may be associated with episodes of acute pancreatitis.

By "bodily fluid" is meant a naturally occurring fluid of the human body such as serum, plasma, blood, urine, mucus, gastric juices, pancreatic juices, or lymph, particularly blood or blood products and urine.

By "disease severity" is meant relative stage of disease progression. Disease severity may be correlated with the impact the disease may have on the patient's overall health or the risk of patient death as a result of disease. The severity of the disease may affect decisions relating to patient treatment subsequent to diagnosis.

By "isolated DNA" is meant DNA that is free of the genes which, in the naturally-occurring genome of the organism from which the DNA of the invention is derived, flank the sequence that constitutes the DNA of the invention. The term therefore includes, for example, a recombinant DNA which is incorporated into a vector; into an autonomously replicating plasmid or virus; or into the genomic DNA of a prokaryote or eukaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence.

By "degenerate variants" of a nucleotide sequence is meant nucleotide sequences which encode the same amino acid sequence as a given nucleotide sequence, but in which at least one codon in the nucleotide sequence is different. Degenerate variants occur due to the degeneracy of the genetic code, whereby two or more different codons can encode the same amino acid.

By "operably linked" is meant that a coding sequence and one or more regulatory sequences (e.g., promoters and/or enhancers) are connected in such a way as to permit gene expression when the appropriate molecules (e.g., transcriptional activator proteins) are bound to the regulatory sequence(s).

By "positioned for expression" is meant that the coding sequence is positioned adjacent to a DNA sequence which directs transcription and translation of the sequence.

By "transformed cell" is meant a cell into which (or into an ancestor of which) has been introduced, by means of recombinant DNA techniques, an isolated DNA molecule encoding (as used herein) a human GP2 polypeptide.

By "polypeptide" is meant any chain of amino acids, regardless of length or post-translational modification (e.g., glycosylation or phosphorylation).

By "conservative amino acid substitution" is meant an amino acid substitution where the native amino acid and the substituted amino acid are of approximately the same charge and polarity. Conservative substitutions typically include, e.g., substitutions within the following groups: glycine, alanine; valine, isoleucine, leucine, methionine; aspartic acid, glutamic acid; asparagine, glutamine; serine, threonine; lysine, arginine; and phenylalanine, tyrosine. In general, such conservative amino acid substitutions do not substantially affect the function of the protein.

By "substantially pure polypeptide" is meant a preparation of GP2 polypeptide which is substantially free from the proteins and other naturally occurring organic molecules with which GP2 is naturally associated. This typically means that GP2 polypeptide constitutes at least 60% of the dry weight of the preparation. Preferably, the preparation is at least 75%, more preferably at least 90%, and most preferably at least 99%, by weight, GP2 polypeptide. A substantially pure GP2 polypeptide may be obtained, for example, by extraction from a natural source (e.g., human pancreas); by expression of a recombinant nucleic acid encoding a GP2 polypeptide; or by chemical synthesis. Purity can be measured and/or obtained by any appropriate method, e.g., column chromatography, polyacrylamide gel electrophoresis, or HPLC.

A protein is substantially free of naturally associated components when it is separated from those contaminants which accompany it in its natural state. Thus, a protein which is chemically synthesized, or produced from a source different from the source from which the protein naturally originates, will be substantially free from its naturally associated components. Accordingly, substantially pure GP2 includes recombinant GP2 synthesized, for example, in vitro in a mammalian cell line, in *E. coli* or another single-celled microorganism, or in insect cells.

By "human GP2" is meant Glycoprotein-2 of the human pancreas. Human GP2, which has the amino acid sequence shown as SEQ ID NO:2, is normally primarily located on the inner leaflet of the zymogen granule (ZG) membranes and the apical plasma membrane of pancreatic acinar cells.

By "antigenic fragment" of GP2 is meant a portion of GP2 which is capable of binding an antibody generated by immunization of a mammal with GP2 or a fragment thereof. Preferably, the antibodies which specifically bind an epitope of the isolated antigenic fragment will also bind the same epitope in the context of the native protein from which the fragment was derived.

By "antibody" is meant an immunoglobulin protein which is capable of binding an antigen. Antibody as used herein is meant to include antibody fragments (e.g. $F(Ab')_2$, FAb', FAb) capable of binding the antigen of interest.

By "binds specifically" is meant high avidity and/or high affinity binding of an antibody to a specific antigen. Antibody binding to its epitope on this specific antigen is stronger than binding of the same antibody to any other epitope, particularly those which may be present in molecules in association with, or in the same sample, as the specific antigen of interest. Antibodies which bind specifically to a polypeptide of interest may be capable of binding other polypeptides at a weak, yet detectable, level (e.g., 10% or less of the binding shown to the polypeptide of interest). Such weak binding, or background binding, is readily discernible from the specific antibody binding to the polypeptide of interest, e.g. by use of appropriate controls.

By "detectably labeled antibody", "detectably labeled GP2" or "detectably labeled GP2 fragment" is meant an antibody (or antibody fragment which retains binding specificity), GP2, or GP2 polypeptide fragment having an attached detectable label. The detectable label is normally attached by chemical conjugation, but where the label is a polypeptide, it could alternatively be attached by genetic engineering techniques. Methods for production of detectably labeled proteins are well known in the art. Detectable labels may be selected from a variety of such labels known in the art, but normally are radioisotopes, fluorophores, enzymes (e.g., horseradish peroxidase), or other moieties or compounds which either emit a detectable signal (e.g., radioactivity, fluorescence, color) or emit a detectable signal after exposure of the label to its substrate. Various detectable label/substrate pairs (e.g., horseradish peroxidase/ diaminobenzidine, avidin/streptavidin, luciferase/luciferin), methods for labelling antibodies, and methods for using labeled antibodies to detect an antigen (such as GP2 or GP2 fragments) are well known in the art (see, for example, Harlow and Lane, eds. (Antibodies: *A Laboratory Manual* (1988) Cold Spring Harbor Laboratory Press, Cold Spring Harbor, N.Y.)).

Other features and advantages of the invention will be apparent from the following detailed description and from the claims.

BRIEF DESCRIPTION OF THE DRAWINGS

FIG. 1 is a representation of the nucleotide sequence and deduced amino acid sequence of the cDNA encoding human GP2 (SEQ ID NO:1).

DETAILED DESCRIPTION

GP2 (Glycoprotein-2) is the major membrane glycoprotein of secretory zymogen granule (ZG) membranes within pancreatic acinar cells (Fukuoka et al. 1990 *Nuc. Acids Res.*, 18:5900; Fukuoka et al. 1991 *Proc. Natl. Acad. Sci., USA*, 88:2898–2902; Fukuoka et al. 1992 *Proc. Natl. Acad. Sci. USA*, 89:1189–1193; Freedman, et al. 1993 *Eur. J. Cell Biol.* 61:229–238; Scheele et al. 1993 *Pancreas* :139–149; Freedman et al. 1994 *Annals N.Y. Acad. Sci.* 713:199–206). In addition to ZG membranes, GP2 is also located in pancreatic acinar cells in rough endoplasmic reticulum, Golgi, trans-Golgi components, condensing vacuoles, apical plasma membranes (APM), basolateral plasma membranes (BPM), and within ZGs and acinar lumina (Scheele et al., 1994 *Pancreas* 9:139–149). GP2 is linked to the membrane of the ZG via a glycosylphosphatidyl inositol-anchor (GPI-anchor) (Fukuoka et al. 1991 *Proc. Natl. Acad. Sci. USA*, 88:2898–2902; Lebel and Beattie 1988 *Biochem. Biophys. Res. Comm.* 254:1189–93) and forms complexes, usually tetrameric complexes, below a pH of about 6.5.

During assembly of secretory granules within the trans-Golgi network (TGN), the low pH of the TGN causes formation of GP2 complexes. These complexes bind to proteoglycans (PG), forming a fibrillar GP2/PG meshwork on the lumenal surface of the ZG. The GP2/PG matrix may function in membrane sorting within the TGN, assembly of ZG membranes, inactivation of ZG membranes during granule storage, and regulation of ZG membrane trafficking at the apical plasma membrane. The GP2/PG matrix may also protect the lumenal aspect of the granule membrane from contact with secretory enzymes contained within the granules and facilitate the specific release of secretory enzymes during exocytosis at the apical plasma membrane.

The enzymes and the acidic milieu contained in the ZG are released into the lumen of the pancreas through exocytosis by acinar cells. The pH at the apical plasma membrane of the acinar cells, and of the pancreatic lumen in general, is maintained at an essentially neutral or alkaline pH by the fluid and bicarbonate secreted by pancreatic ductal cells. The increased pH at the apical plasma membrane (relative to the acidic pH within the ZG) optimizes the conditions for enzymatic cleavage of the GPI anchor of GP2, resulting in release of GP2 and GP2/PG complexes from the apical membrane. (Scheele et al. (1994) *Pancreas* 9:139–149). The form of GP2 produced by GPI-anchor cleavage is termed globular GP2 (gGP2).

Cloning of the human GP2 gene

A human pancreatic cDNA library was constructed in lambda gt10. Approximately $2\times10^5$ clones obtained in the cDNA library were screened with a radioisotope-labeled probe derived from the rat GP2 sequence (Fukuoka and Scheele, 1990, *Nuc. Acids Res.* 18:5900). The probe was a EcoRI-EcoRI 2.0 kb fragment of the rat GP2 cDNA and includes a complete open reading frame for the protein. Conditions for prehybridization, hybridization and filter washes were as described in Fukuoka and Scheele, 1990, *Pancreas* 5:1–7. Briefly, after transfer of the clones to nylon filters, the double stranded DNAs were denatured twice in 0.5N NaOH and neutralized with 1M Tris-HCl, pH 7.5. The filters were then dried at room temperature. Hybridization screening was performed under stringent conditions as described in Sambrook et al. (*Molecular Cloning—A Laboratory Manual*, Second Ed. (1989), Cold Spring Harbor Laboratory, Cold Spring Harbor, N.Y., page 9.52) with final washes as follows: 1) three washes in 0.4×SSC, 0.1% sodium-dodecyl sulfate (SDS) at 65° C., 2) three washes in 0.2×SSC and 0.1% SDS at 65° C. for 30 minutes each. The semi-dried filters were wrapped in plastic bags and exposed to X-ray film in the presence of an intensifying screen for 24 hours at −70° C.

Ten clones which hybridized with the rat GP2 cDNA probe were purified. The size of the cDNA inserts in the vectors was checked by polymerase chain reaction (PCR) using primers designed to hybridize outside of the insertion site. Three clones having the largest inserts were selected for further study. These clones showed identical restriction patterns when cut with several different restriction enzymes. A single clone was then selected for sequence analysis. The insert in this clone was excised from the lambda vector and subcloned into the EcoRI site of the Bluescript™ plasmid vector. The nucleotide sequence of each strand of the insert was determined using the dideoxy termination method described by Tabor and Richardson, 1987, *Proc. Natl. Acad. Sci. USA* 84(14):4767–4771. The inserts of nested sets of overlapping clones made by ExoIII/ExoVII deletions (Yanisch-Perron et al., 1985, *Gene* 33:351–359) were sequenced in order to obtain the entire human GP2 cDNA sequence.

The nucleotide sequence for the human GP2 cDNA (SEQ ID NO:1) was translated and compared to the sequences for rat GP2 and dog GP2 using the DNASIS program. The human GP2 cDNA encodes a distinctly smaller GP2 protein (SEQ ID NO:2) compared to the rat and dog homologs. The difference is not attributable to an artifact such as mRNA truncation during library construction, since human GP2 includes sequences corresponding to both the signal peptide and the carboxy terminus of these homologs. The segment absent in human GP2 corresponds to amino acids 1 to approximately 150 of the "mature" rat sequence and an even longer portion of the dog sequence.

Expression of GP2 in eukaryotic/prokaryotic hosts

The human GP2 cDNA insert was excised from the Bluescript™ construct described above and subcloned into the BamHI site of the prokaryotic expression vector pET16B (Novagen) using a BamHI linker. Due to the limited choice of cloning sites, a 38 amino acid extension derived from the in-frame sequence of the 5' non-coding sequence of human GP2 was inserted 5' of the GP2 cDNA insert. In addition, a 23 amino acid extension derived from the pET16 vector, which contains the initial methionine, a polyhistidine tag, and a hinge region to connect these sequences to GP2, was inserted 5' to the human GP2 cDNA insert containing the 38 amino acid extension. Thus, the protein expressed from this vector is a recombinant hybrid human GP2 protein containing an artificial 61 amino acid extension at the N-terminal portion of the molecule.

This artificial region is not expected to affect the ability of the GP2 protein to compete for antibody binding with native GP2 found in bodily fluids such as serum or urine. However, antibodies generated to this particular recombinant hybrid GP2 protein may react with this artificial N-terminal portion of the recombinant protein, rather than with the GP2 portion. Antibodies which specifically bind this artificial N-terminus would be undesirable for use in detecting native GP2 in the diagnostic assays described herein.

Antibodies which bind a non-GP2 epitope of recombinant hybrid GP2 (or chemically modified GP2) may be selected against by screening the antibodies for the ability to bind to GP2 (or a fragment of GP2) which does not contain any non-GP2 epitopes. Antibodies which are capable of binding both the GP2 fusion protein and GP2 which does not contain a non-GP2 epitope (such as the artificial N-terminal sequences described above) can be used in assays to detect GP2 in samples of bodily fluids. Alternatively, antibodies which bind an artificial epitope of recombinant or chemically modified GP2 may be eliminated by adsorbing the antisera to a sample which contains the artificial epitope, but does not contain epitopes of naturally-occurring GP2. For example, where the GP2 fusion protein described above is used to generate antibodies, the antisera may be adsorbed with a protein which contains the same artificial N-terminus fused to an immunogenically unrelated protein, such as β-galactosidase.

The expression plasmid constructed as described above was introduced into the host bacterial strain DE3 (Novagen). Transformed cells containing the expression plasmid were incubated at 37° C. When the transformed cells entered logarithmic phase, 0.1 mM IPTG was added to the culture. After incubation at 37° C. for an additional 5 hrs, the cells were collected and lysed by sonication. The cell debris was pelleted, and the supernatant was collected and loaded onto an affinity column having a nickel moiety. Use of this affinity column to purify the recombinant protein takes advantage of the polyhistidine tag present in the recombinant molecule. The polyhistidine region binds the nickel and can be easily released by shifting the pH. The bound recombinant protein was eluted and analyzed by SDS-PAGE. A single band of 49.5 kD was observed. Because the predicted molecular weight of human GP2 is 42.5 kD and the extension peptide is approximately 7 kD, this 49.5 kD band was of the expected molecular weight.

Those skilled in the field of molecular biology will understand that any of a wide variety of expression systems in addition to that exemplified above may be used to provide recombinant GP2 protein, or fragments thereof, by expression of either all or a portion of the cDNA described herein. The precise host cell used is not critical to the invention. The GP2 protein may be produced in a prokaryotic host (e.g., *E. coli*) or in a eukaryotic host (e.g., yeast (*Saccharomyces cerevisiae*) or mammalian cells, e.g., COS-6M, COS-7, NIH/3T3, Chinese hamster ovary cells). Such cells are available from a wide range of sources (e.g., the American Type Culture Collection, Rockville, Md.). The method of transformation or transfection, and the choice of expression vehicle, will depend on the host system selected. Prokaryotic cell transformation, prokaryotic expression systems, and methods are described in, e.g., Sambrook et al. (*Molecular Cloning: A Laboratory Handbook* (1989) Cold Spring Harbor Laboratory, Cold Spring Harbor, N.Y.). Mammalian cell transfection, expression systems, and methods are described in, e.g., Ausubel et al. (*Current Protocols in Molecular Biology*, John Wiley & Sons, New York, 1989). In general, expression vehicles may also be chosen from those provided, e.g., in *Cloning Vectors: A Laboratory Manual* (P. H. Pouwels et al., 1985, Supp. 1987).

An exemplary mammalian expression system uses the Chinese hamster ovary (CHO) cells (ATCC Accession No. CCL 61) transfected with a pcDNAI/NEO expression vector (InVitrogen, San Diego, Calif.). pcDNAI/NEO provides an SV40 origin of replication which allows replication in mammalian systems, a selectable neomycin gene, and SV40 splicing and polyadenylation sites. DNA encoding the human GP2 protein, or an appropriate fragment thereof (as described above), is inserted into the pcDNAI/NEO vector in an orientation designed to allow expression. NIH/3T3 cells (ATCC Accession No. 1658) may also be used in conjunction with the pcDNAI/NEO expression vehicle.

Alternatively, cDNA encoding human GP2 (or GP2 fragment or analog) may also be cloned into an expression vector which includes the dihydrofolate reductase (DHFR) gene. Integration of the plasmid and, therefore, the cDNA encoding human GP2 into the host cell chromosome is selected for by inclusion of 0.01–300 μM methotrexate in the cell culture medium (as described in Ausubel et al., supra). This dominant selection can be accomplished in most cell types. Recombinant protein expression can be increased by DHFR-mediated amplification of the transfected gene by methods known in the art (e.g., Ausubel et al. supra), which generally involve extended culture in medium containing gradually increasing levels of methotrexate. DHFR-containing expression vectors commonly used for this purpose include pCVSEII-DHFR and pAdD26SV(A) (described in Ausubel et al., supra). Preferably, the host cell used with such DHFR-containing expression vectors is a DHFR-deficient cell line, such as a DHFR-deficient CHO cell line (e.g., ATCC Accession No. CRL 9096).

A number of other vectors suitable for stable transfection of mammalian cells are available to the public, e.g., see Pouwels et al. (supra); methods for constructing such cell lines are also well known, e.g., see Ausubel et al. (supra).

Expression of recombinant human GP2 (e.g., produced by any of the prokaryotic or eukaryotic expression systems described herein) may be assayed by immunological procedures, such as Western blot, immunoprecipitation analysis of recombinant cell extracts, or immunofluorescence (using, e.g., the methods described in Ausubel et al., supra). The recombinant GP2 protein or GP2 protein fragment may be isolated and used directly in an immunoassay of the invention (described below), or may be used as an immunogen to generate antibodies for use in an immunoassay of the invention.

Isolation and purification of human GP2 protein

Once the recombinant human GP2 protein (or fragment thereof) is expressed, it may be isolated by various chromatographic and/or immunological methods well known in the art (see, for example, Sambrook et al., *Molecular Cloning: A Laboratory Handbook*, (1989) Cold Spring Harbor Laboratory, Cold Spring Harbor, N.Y.). For example, an anti-human GP2 protein antibody may be attached to a column and used to isolate intact GP2 protein or GP2 protein fragments. Lysis and fractionation of GP2 protein-containing cells prior to affinity chromatography may be performed by standard methods (see, e.g., Ausubel et al., supra). Once isolated, the recombinant protein can, if desired, be further purified, e.g., by high performance liquid chromatography (see, e.g., Fisher, *Laboratory Techniques In Biochemistry And Molecular Biology*, Work and Burdon, eds., Elsevier, 1980).

Alternatively, recombinant GP2 may be expressed as a fusion protein and isolated by exploiting particular characteristics of the artificial portion (i.e. the non-GP2 portion) of the fusion protein. For example, recombinant human GP2 protein (or a fragment of human GP2 protein) may be expressed using the glutathione-S-transferase (GST) sequence fused to the pGEX vector (Pharmacia; Smith and Johnson, 1988, *Gene* 67:31–40) containing all or a portion of the human GP2 cDNA. The recombinant human GP2 protein can be released from the GST sequences present in the resultant fusion protein by cleavage of the fusion protein with specific proteases. Alternatively, and as exemplified above, a recombinant human GP2 fusion protein containing a polyhistidine tag can be produced. The GP2 fusion protein may then be isolated by binding of the polyhistidine tag to an affinity column having a nickel moiety which binds the polyhistidine region with high affinity. The fusion protein may then be eluted by shifting the pH within the affinity column.

Human GP2 protein of the invention, or human GP2 protein fragments, can also be produced by chemical synthesis (e.g., by the methods described in *Solid Phase Peptide Synthesis*, 2nd ed., 1984, The Pierce Chemical Co., Rockford, Ill.).

Production of antibodies which specifically bind human GP2

Antibodies specific for human GP2, or a fragment of human GP2, may be produced as follows. A polypeptide corresponding to all or part of human GP2 is produced by expression of all or a portion of the cDNA encoding human GP2 in a host cell as described above. Alternatively, human GP2, or peptide fragments thereof, may be produced by synthetic chemistry using standard techniques. Where desired, the peptides may be coupled to a carrier protein or other adjuvant to increase immunogenicity. The peptide or peptide-carrier is mixed with Freund's adjuvant and injected into animals (e.g., mice, guinea pigs, rabbits) to produce polyclonal antibodies. Monoclonal antibodies which specifically bind recombinant human GP2 protein, or fragments thereof, may be generated using standard hybridoma technology (see, e.g., Kohler et al., 1975, *Nature* 256:495; Kohler et al., 1976, *Eur. J. Immunol.* 6:292; Kohler et al. 1976 *Eur. J. Immunol.* 6:511; Hammerling et al. in *Monoclonal Antibodies and T Cell Hybridomas*, (1981) Elsevier, N.Y.; Ausubel et al., supra; Harlow and Lane, eds.; *Antibodies: A Laboratory Manual*, (1988) Cold Spring Harbor Laboratory, Cold Spring Harbor, N.Y.). Once produced, antibodies may be tested for specific binding to human GP2 protein by Western blot, immunoprecipitation analysis, or other methods known in the art (see Ausubel et al., supra; Harlow and Lane, supra). Antibodies so produced may be used in the immunoassays of the invention for detection of human GP2 in a sample, as described herein.

Two anti-GP2 monoclonal antibodies were generated using a precipitate from human pancreatic juice as an immunogen. The precipitate was prepared by collecting pure human pancreatic juices from patients whose pancreas had been removed surgically due to the presence of a pancreatic cancer. The pancreas were cannulated to drain the juice and the juice collected at room temperature. The pancreatic juice was then cooled and stored at $-20°$ C. until use. When a sufficient amount of juice had been obtained, the frozen juice was placed in a flask and heated to about 100° C. (boiled) for 10–15 mins. A large precipitate appeared in the flask. This precipitate was sedimented by centrifugation at 3500 rpm. The supernatant was transferred into a fresh flask and 2 volumes to 2.5 volumes of ethanol added. This mixture was then allowed to stand at 4° C. for 2–4 hrs. The precipitate which resulted was collected by centrifugation (approximately 10,000 rpm). Analysis of the precipitate on SDS page revealed bands of 70 kD and 100 kD molecular weight, as well as large aggregates with higher molecular weights. The large aggregates were removed by using a sizing column (SEPHADEX G100™), and fractions containing the 70 kD and 100 kD proteins were pooled and lyophilized. The antigen solution for immunization was prepared by resuspending this lyophilized material.

Murine monoclonal antibodies which reacted to the 70 kD and 100 kD molecules were prepared by methods well known in the art using the antigen solution described above. Two antibodies, 7A4 and 3A9, were identified. Both of these antibodies bind to both the 70 kD and 100 kD proteins with approximately equal affinity. Further characterization of the antibodies revealed that the 3A9 antibody binds to a sugar moiety of these proteins. In addition to binding both the 70 kD and 100 kD proteins, the 7A4 antibody also binds to the 49.5 kD recombinant human GP2 protein described above. Therefore, the 70 kD and 100 kD proteins obtained from pancreatic juice may be glycosylated forms of human GP2 protein.

Further studies showed that the 7A4 antibody binds to human, monkey, and cow pancreatic tissue at the apical side of the pancreatic cells as observed by light microscopy. The 7A4 antibody did not bind to the intralobular space, pancreatic ducts, or the islets of Langerhans. Moreover, the 7A4 antibody did not bind to dog zymogen granule membranes or to the human parotid gland, a negative control for GP2 binding.

Identification of patients

Patients who present with the classical symptoms of acute pancreatitis or have a medical history which indicates susceptibility to pancreatitis may be tested with the methods of the invention. Classic symptoms of acute pancreatitis include non-fluctuating midepigastric pain which radiates directly through to the back and may last for many hours to many days. Epigastric pain may be relieved by sitting and leaning forward. Breathing may also be painful if there is an associated pleural effusion and pleuritis. The majority of patients experience nausea and vomiting when the pain reaches its maximum and may experience shock and obtundation if the episode persists for more than several hours. Many patients present with a fever, but have no demonstrable infection. The abdomen is frequently distended and bowel sounds are decreased or absent due to a secondary ileus. Physical examination usually reveals a soft abdomen or only mild voluntary guarding. If severe hemorrhagic pancreatitis has developed, the pain may be excruciating, with marked guarding and even rebound tenderness. In recurrent pancreatitis, a mass may be palpated, indicating the presence of a pseudocyst.

In chronic pancreatitis, episodes of severe abdominal pain similar to that in acute pancreatitis develop, although bouts of only moderately severe pain also occur. These episodes of pain typically are separated by asymptomatic periods. In later years, the disease becomes more established, and the episodes of pain may persist or recur daily for weeks or months. Very severe pain may last 2 to 14 days and require continuous administration of narcotics. When greater than 90% of the pancreatic tissue is destroyed, pancreatic insufficiency leads to malabsorption that may be diagnosed by increased fatty stools.

Patients with a history of alcoholism, biliary tract disease, or hyperlipoproteinemia should also be tested for development of pancreatitis. Other appropriate patients for pancreatitis testing include those who have a family history of hereditary pancreatitis or pancreatic carcinoma, have suffered an accidental trauma which may involve the pancreas, or have experienced a recent infection which may involve the pancreas, such as an infection caused by mumps virus, S. typhi, or streptococci. Patients who are receiving drugs implicated in the induction of pancreatitis should also be tested.

The diagnostic method of the subject invention may be used to detect either acute or chronic pancreatitis prior to, or after the onset of, clinical symptoms associated with pancreatitis. Because GP2 is passed from the blood circulation into the urine, GP2 levels may be elevated in urine for longer periods of time than in the bloodstream. Thus, elevations in GP2 may be detected in blood during earlier stages of pancreatitis and in both urine and blood during later stages of the disease. Moreover, elevations of GP2 may be detected in urine when GP2 increases are no longer detectable in blood. Preferably, both blood and urine samples will be screened for the presence of GP2 in order to provide the most accurate diagnosis.

The method of the subject invention facilitates diagnosis of pancreatitis prior to or coincident with the onset of clinical symptoms (e.g., epigastric pain). For example, the method of the subject invention may provide a diagnosis of pancreatitis prior to (e.g., 12–24 hrs or even 24–48 hrs before) onset of clinical symptoms. Furthermore, the method of the subject invention allows the clinician to provide an accurate diagnosis of pancreatitis even several hours after cessation of clinical symptoms (e.g., up to 5, more preferably up to 8, even more preferably up to 12, and more preferably up to 18 hrs), up to one or a few days (e.g., 2 days, preferably 3 to 7 days) after cessation of clinical symptoms. The diagnostic method of the subject invention is particularly advantageous over prior art diagnostic methods for pancreatitis since, due to its high net negative charge, the half-life of GP2 in bodily fluids is significantly longer than that of proteins normally used as indicators of a pancreatitis condition (e.g. amylase, lipase, trypsinogen).

Detection of GP2 in bodily fluids

GP2 may be detected in bodily fluids as a monomer, as a complex of GP2 molecules, and/or as a complex of GP2 and proteoglycan. After determining that a patient should be tested for pancreatitis, a sample of bodily fluid, preferably blood, serum, or urine, is collected from the patient. Samples of blood, serum, or urine between a few microliters and a few milliliters (e.g. between about 25 µl and 1,000 µl, up to about 5 ml to 10 ml) is sufficient for detection of GP2, which is present in blood or urine at levels ranging from picograms to nanograms per ml. Appropriate control samples for the assay include blood, serum, or urine collected from individuals who do not have pancreatitis (negative control), or samples which contain a known, predetermined amount of GP2 (positive control).

The samples may be treated in a variety of ways so as to enhance detection of GP2. For example, where the sample is blood, it may be preferable to remove the red blood cells from the sample (e.g., by centrifugation) prior to assaying. This treatment may serve to reduce the non-specific background levels of binding of the human GP2 specific antibody. Detection of GP2 may also be enhanced by concentrating the sample using procedures well known in the art (e.g. acid precipitation, alcohol precipitation, salt precipitation, hydrophobic precipitation, filtration (using a filter which retain molecules greater than 30 kD, e.g. Centrim 30™), affinity purification). Preferably, the pH of the test and control samples will be adjusted to, and maintained at, a pH which approximates neutrality (i.e. pH 6.5–8.0). Extremes of pH should be avoided. This pH adjustment will prevent GP2 complex formation, providing a more accurate quantitation of the amount of GP2 in the sample. Where the sample is urine, it may be preferable both to adjust the pH of the sample and to concentrate the sample to enhance for GP2 detection.

The antibody used in the assay may either be a polyclonal or monoclonal antibody, and will usually be of the IgG or IgM class. Antibody fragments (e.g. Fab'$_2$, Fab') which specifically bind human GP2 may also be used. The antibody will preferably bind an epitope of GP2 which is available for antibody binding when GP2 is present as a monomer, a complex (such as a tetrameric GP2 complex), and/or a complex of GP2 with proteoglycans. The antibody used will preferably not bind to the GPI-anchor portion of GP2, as such antibodies may be cross-reactive with other GPI-anchor proteins and may not detect globular GP2. In addition, the antibody used in the assay will preferably not bind to a non-native portion of a recombinant GP2 molecule used as the immunogen during antibody production.

The diagnostic assay may be performed in solution or may use a solid (insoluble) support (e.g. polystyrene, nitrocellulose, or beads), using any standard methods (e.g., as described in *Current Protocols in Immunology*, Coligan et al., ed.; John Wiley & Sons, New York, 1992). Typical methods include ELISAs (enzyme-linked immunosorbent assays), IRMAs (immunoradiometric assays), and RIAs (radioimmunoassays). Where the assay is performed in solution, the test and control samples are each incubated with an anti-human GP2 antibody for a time period sufficient to allow formation of GP2-antibody complexes, preferably between about 0.1 hrs up to 24 hrs, or more. The anti-human GP2 antibody may comprise a detectable label (e.g. radionuclide, fluorescer, or enzyme). The sample is then treated to separate GP2-antibody complexes from excess, unreacted anti-human GP2 antibody (e.g. by addition of anti-immunoglobulin antiserum followed by centrifugation [e.g., 1000×g for 7 min] to precipitate the antiserum/antigen complexes, or by binding to an affinity surface such as a second, unlabelled anti-GP2 antibody fixed to a solid substrate such as Sepharose or a plastic well). Detection of antibody bound to GP2 may be achieved in a variety of ways well known in the art. If necessary, a substrate for the detectable label may be added to the sample.

Where the assay uses a solid support, the support will have a capture reagent bound to the support surface. Capture reagents are molecules capable of specifically binding human GP2, thus facilitating the stable, wash-resistant binding of GP2 present in the sample to the solid support. Suitable capture reagents include antibodies which specifically bind human GP2, anti-human GP2 antibody fragments, or anti-idiotype antibodies which specifically bind to the anti-GP2 antibody. Alternatively, the solid support itself may bind GP2 directly through the charged properties of the support surface, thus taking advantage of the highly negatively charged nature of the GP2 molecule. Methods for binding antibodies and other capture reagents to solid supports are well known in the art. After binding of the capture reagent to the support, the support may be treated with a blocking agent (such as bovine serum albumin), which binds to the support in areas not occupied by the antibody or other capture reagent. Such blocking treatment reduces nonspecific binding.

The test and control samples are each incubated with the solid support for a time sufficient for binding of GP2 to the capture reagent. After incubation, the reacted samples may be washed to remove unbound or non-specifically bound material. An isotonic buffer, such as phosphate-buffered saline, may be employed in the washing step. Preferably, the washing step will not cause dissociation of GP2-capture reagent complexes. An antibody which specifically binds human GP2 is then incubated with the GP2-capture reagent complexes. Where the capture reagent is an anti-human GP2 antibody, the second antibody preferably binds to an epitope different from the epitope bound by the first antibody. The second antibody used to detect GP2 bound to the support may be detectably labeled to facilitate detection of GP2-first antibody-second antibody complexes. Alternatively, a third detectably labeled antibody which specifically binds the second antibody may be used to detect the GP2-first antibody-second antibody complexes.

To determine whether the patient from whom the test sample was collected has pancreatitis, the level of anti-GP2 antibody binding in the test sample is compared to the level of anti-GP2 antibody binding in the negative and/or positive control samples. A level of antibody binding in the test sample significantly greater than the level of antibody binding in the negative control sample, or at least equal to the level of antibody binding in the positive control sample, indicates that the patient has pancreatitis.

Alternatively, GP2 may be detected by using a competitive binding assay. The test and control samples are incubated with the anti-GP2 antibody as described above, to allow for formation of GP2-antibody complexes. The antibody may be fixed to a solid surface or in solution. After washing to remove unbound material from the precipitated antibody-GP2 complexes or from the solid support (if any) to which the antibody is fixed, the samples are then incubated with a standard amount of detectably labeled GP2, detectably labeled recombinant hybrid GP2, or a detectably labeled fragment of GP2 which retains the ability to compete with native GP2 for binding sites on the anti-GP2 antibody. Binding is detected by standard means: e.g., by measuring the amount of label associated with (a) the solid support (if any), or (b) the precipitated antigen/antibody complexes. A lower level of binding of the detectably labeled GP2 in the test sample than in the negative control indicates the presence of elevated GP2 in the test sample, and thus a diagnosis of pancreatitis.

Alternatively, the binding of the second GP2 molecule used in the competitive binding assay (i.e. the GP2 introduced into the test sample after incubation of the test sample with the anti-GP2 antibody), may be measured by means of an epitope present on the second GP2 molecule which is absent in native GP2 derived from a sample of bodily fluid. For example, the second GP2 molecule may be a recombinant fusion protein which retains the ability to bind competitively to the antibody used in the assay. Binding of GP2 fusion protein to the anti-GP2 antibody may then be detected by incubating the sample with a detectably labeled second antibody which specifically binds the fusion protein and does not bind native GP2. The recombinant human GP2 fusion protein described above (human GP2 containing a 61 amino acid N-terminal extension) is an example of such a fusion protein which may be used in this detection method, since antibodies which specifically bind to the 61 amino acid non-native portion of this recombinant molecule would not be expected to bind to native GP2. Examples of other epitopes which may be introduced into a GP2 fusion protein include epitopes for use as targets for chemical modification and epitopes which have an altered amino acid sequence relative to naturally-occurring GP2 (to provide a peptide epitope absent in native GP2).

The severity of pancreatitis may be determined by quantitating the amount of GP2 in the test sample, or by determining the relative amount compared to standard controls. For example, quantitation of GP2 may be achieved by comparing the level of antibody binding in the test sample to the level of antibody binding in one or more identically treated control samples containing known amounts of GP2, or by comparing the test sample readout to a table of standard values. Where a competitive binding assay is employed, the levels of binding of detectably labeled GP2 may be correlated with the levels of binding of the labeled protein in samples having a known amount of GP2. The amount of GP2 present in the test sample may then be correlated with a degree of disease severity and patient prognosis by reference to these controls. Quantitation of GP2 in the test sample may alternatively be achieved by precipitation of the GP2-antibody complexes from solution and comparison of the amount of protein in the test sample precipitate relative to precipitates of control sample(s) having a known amount of GP2.

The materials for performing the diagnostic assay may be provided as a kit having instructions for use. The kit may be composed in part of a vessel containing a first antibody which specifically binds to human GP2. This kit may further include a second vessel which contains a detectably labeled second antibody which binds to the anti-human GP2 antibody contained in the first vessel or which binds to GP2 at an epitope different from that bound by the first antibody. Either the first or the second antibody is optionally fixed to a solid substrate (e.g., a microtitre well or Sepharose beads). One of the antibodies may be detectably labeled with an enzyme, in which case the kit further includes a third vessel containing a substrate for the enzyme. The kits exemplified above are useful in, for example, detecting the presence of GP2 in a sample of human bodily fluid.

Alternatively, the kit may be composed of a first vessel which contains an antibody which specifically binds to human GP2, and a second vessel which contains detectably labeled human GP2; or a first vessel containing an anti-human GP2 antibody and a second vessel containing a detectably labeled fragment of human GP2, where the fragment has an epitope to which the antibody specific for human GP2 specifically binds. The antibody may be fixed to a solid support, or in solution. These types of kits are useful in, for example, competition assays to detect the presence of human GP2 in a sample of bodily fluid.

An exemplary kit may include a dipstick, to the surface of which is bound an antibody which specifically binds human GP2. The dipstick is inserted directly into a test sample (e.g., serum) for a period of time sufficient to permit binding of GP2 to the antibody bound to the dipstick. The dipstick may be then withdrawn and, if necessary, washed to remove nonspecifically bound material. The dipstick is then inserted into a container containing a detectably labeled second antibody which specifically binds human GP2. After incubation for a time sufficient for binding of the second antibody to the GP2-antibody complexes, the dipstick may be washed and binding of the second antibody detected by standard means. Where necessary for detection of the second antibody, the dipstick may be inserted into a second container containing a reagent which activates the detectable label on the second antibody.

As will be apparent to one of ordinary skill in the art upon reading the present specification, many modifications can be made to the subject invention without departing from the spirit or scope of the dependent claims. It is also to be understood that the terminology used herein is for the purpose of describing particular embodiments only, and is not intended to be limiting.

What is claimed is:

1. An isolated DNA encoding a polypeptide comprising the contiguous amino acid sequence of SEQ ID NO:2, said polypeptide being substantially shorter than rat GP2.

2. The DNA according to claim 1, wherein said DNA is cDNA.

3. The DNA according to claim 1, wherein said DNA is operably linked to a promoter sequence for expression of said polypeptide.

4. An isolated DNA comprising the contiguous nucleotide sequence of SEQ ID NO:1, or a degenerate variant thereof.

5. An isolated DNA which encodes a polypeptide consisting of the contiguous amino acid sequence of SEQ ID NO:2.

6. The DNA of claim 4, wherein said DNA hybridizes under stringent hybridization conditions to a DNA probe, the sequence of which is complementary to the contiguous nucleotide sequence of SEQ ID NO:1.

7. A transformed cell containing an isolated DNA encoding a polypeptide comprising the contiguous amino acid sequence of SEQ ID NO:2.

8. A method of producing a polypeptide comprising:
   culturing a cell transformed with an isolated DNA encoding a polypeptide comprising the contiguous amino acid sequence of SEQ ID NO:2, said DNA being positioned for expression in said cell, said culturing being under conditions for expressing said DNA; and isolating said polypeptide.

9. The DNA of claim 4, wherein the nucleotide sequence of said DNA comprises the contiguous nucleotide sequence of SEQ ID NO:1.

10. The cell of claim 7, wherein the amino acid sequence of said polypeptide consists of the contiguous amino acid sequence of SEQ ID NO:2.

11. The cell of claim 7, wherein said DNA comprises the contiguous nucleotide sequence of SEQ ID NO:1.

12. The method of claim 8, wherein the amino acid sequence of said polypeptide consists of the contiguous amino acid sequence of SEQ ID NO:2.

13. The method of claim 8, wherein said DNA comprises the contiguous nucleotide sequence of SEQ ID NO:1.

* * * * *